US005746024A

United States Patent [19]
Rice et al.

[11] Patent Number: 5,746,024
[45] Date of Patent: May 5, 1998

[54] PROCESS FOR PRODUCING LARGE QUANTITIES OF VIABLE TRUE SEED FROM GARLIC

[75] Inventors: Robert M. Rice; Kevin B. Brink, both of Turlock; David J. Hansen, Modesto, all of Calif.

[73] Assignee: Rogers Foods, Inc., Turlock, Calif.

[21] Appl. No.: 675,604

[22] Filed: Jul. 3, 1996

[51] Int. Cl.⁶ .......................... A01B 79/00; A01C 1/00; A01C 1/06; A01C 21/00; A01G 13/02
[52] U.S. Cl. ............................ 47/58; 47/57.6; 47/DIG. 1
[58] Field of Search .......................... 47/58, 57.6, DIG. 1

[56] References Cited

U.S. PATENT DOCUMENTS

| | | | |
|---|---|---|---|
| 5,097,624 | 3/1992 | Klayman et al. | 47/31 |
| 5,270,039 | 12/1993 | Yoo et al. | 424/93 |
| 5,367,111 | 11/1994 | Ohsumi et al. | 800/200 |

OTHER PUBLICATIONS

Pooler and Simon, "True Seed Production in Garlic", *Sexual Plant Reproduction* (1994) 7:282–286.
Walkey, et al., "Production of Virus–Free Garlic *Allium sativum L.* and Shallot *A. Ascalonicum L.* By Meristem–Tip Culture," *Journal of Horticultural Science* (1987) 62 (2):211–220.
Maksoud, et al., "Garlic Tissue Culture Organogenesis in Callus Culture," *Egypt Journal of Horticultural* (1983) 10 (2):107–114.
Etoh T., "Germination of Seeds Obtained From a Clone of Garlic, *Allium sativum L.*", Proc. Japan Acad., 59, Ser. B., (1983).
L. Bos "Viruses and Virus Diseases of *Allium Species*" Acta Horticulurae (1982) 127:11–29.
Ayuso, et al., "The Elimination of Garlic Viruses by Thermotherapy and/or Tissue Culture," *Cell Biology International Reports*, (1981) 5 (9):835.
"Growing Garlic in California," *Division of Agricultural Sciences,* University of California Leaflet 2948, Dec. 1976.
Konvicka, et al., "Investigation into the causes of pollen sterility in *Allium sativum L.*" (1978).
Gamborg et al., "Plant tissue culture media", *In Vitro* (1976) 12 (7):473–478.
"Onion Production in California," *Division of Agricultural Sciences,* University of California Leaflet 4097, pp. 42–43.

Nome et al., Obtención De Plantas De Ajo (*Allium Sativum L.*) Libres De Virus Mediante Elcultivo De Meristemas Apicales, Phyton. Int. Journal of Exp. Botany, 41 (½):139–151, 1981.
Peiwen et al., Strategy for the Use of Virus–Free Seed Garlic In Field Production, Acta Horticulturae, 358:306–311, Mar. 1994.
Walkey et al., Production of Virus–Free Garlic (*Allium Sativum L.*) and Shallot (*A. Ascalonicum L.*) By Meristem–Tipculture, J. Hortic. Sci., 62(2): 211–220, 1987.
Pooler M.R. & P.W. Simon; True Seed Production In Garlic; Sex Plant Reprod (1994) 7:282–286.
Bos; Viruses and Virus Disease of *Allium* Species; Actica Horticulturae; 127, 1982 (11–29).
Peiwen et al.; Strategy for the Use of Virus–Free Seed Garlic in Field Production; Acta Horticulturae, Mar. 1994; 358:307–311.
Dijk, P. van; Virus Diseas of *Allium* Species and Prospects for their Control; Acta Horticulturae, Mar. 1994, 358:299–306.
Chenst Huangj.; Rapid Clonal Propagation and Virus–Elimination of Garlic, Acta Hortic Sin; 18(3): 1991; 245–250.
Bhojwani et al.; Production of Virus–Free Garlic *Allium–Satiuum,* Sci Hortic (Amst), 18(1); 1982; 39–44.
Bhojwani S.S.; In–Vitro Propagation of Garlic *Allium–Sativum* By Shoot; Sci Hortic; 13(1); 1980; 47–52.
Nome et al.; Production of Virus–Free Garlic Plants (*Allium sativum L.*) By Growing Apicalmeristems Propagation, Argentina; Phyton; International J. Exp. Bot. (1981); 41(½): 139–151.
Kudou et al.; Breeding and Propagation of Good Sedlings of Garlic by Tissue Culture, III Effects of Plant Growth Regulators and Sampling Positions on Organ Formation of Garlic; Kagawa Daigaku Nogakubu Gakujutsu Hokoku, 1985, 47(1), 15–22.

*Primary Examiner*—David T. Fox
*Assistant Examiner*—Kent L. Bell
*Attorney, Agent, or Firm*—Whyte Hirschboeck Dudek

[57] ABSTRACT

Large quantities of true seed is obtained from garlic using a process that involves the growing of a garlic parent plant from a virus-free garlic propagule under virus-free conditions such that the garlic parent plant remains free from virus infection and in particular infection by the onion yellow dwarf virus.

6 Claims, No Drawings

PROCESS FOR PRODUCING LARGE QUANTITIES OF VIABLE TRUE SEED FROM GARLIC

FIELD OF THE INVENTION

The present invention relates to viable, true seed of garlic and a method of producing large quantities of the same.

BACKGROUND OF THE INVENTION

To date, garlic has been commercially produced using asexual propagation techniques, i.e. reproduction without the union of gametes, because production of large quantities of viable true seed is not possible. As a result of selection over thousands of years, the amount of genetic variation present in cultivated garlic has been severely limited. In addition, asexual reproduction has led to virus infections, such as infection by the onion yellow dwarf virus, in virtually all cultivated garlic world-wide. As a result, expensive and time consuming tissue culture techniques have been required to produce and maintain asexually reproduced garlic lines that are not virus infected. Another difficulty of an asexually propagated crop such as garlic is that the production of propagation stock is an expensive and difficult undertaking. Long term storage of propagation stock is not practical and it must be planted and grown every year.

Viable true seed (i.e., the embryo and associated food storage and protective structure formed by sexual reproduction that is capable of germination) and the development of methods to produce large quantities of viable true seeds from garlic can overcome each of the difficulties identified above. Specifically, the sexual recombination of the genes of different garlic lines can generate a virtually unlimited amount of genotypic variability. This allows for the creation of a large number of potential commercial vegetatively propagated varieties of garlic using classical plant breeding techniques. Also, these breeding techniques can lead to varieties of garlic that possess the necessary genetic makeup to allow direct seeding of true seed to grow the commercial crop. In addition, when true seeds are produced, they do not carry the viruses that have accumulated in the asexually propagated varieties. Moreover, the amount of planting material required for the commercial production of garlic would be reduced by several orders of magnitude if true seed were utilized. This reduction in the amount of planting material would in turn reduce the amount of land necessary for growing the garlic propagation stock.

SUMMARY OF THE INVENTION

This invention relates to a process for the production of large quantities of viable true seed from garlic that involves the growing of a garlic parent plant from a virus-free garlic propagule under virus-free conditions such that the garlic parent plant remains free from virus infection, and in particular free from infection by the onion yellow dwarf virus.

Each individual plant grown from the true seed is a potential novel asexual variety and/or the potential sexual progenitor of additional novel varieties of garlic. In addition, the sexually reproducing varieties have the potential of developing varieties that can be grown directly from true seed in one growing season. Both types of varieties, however, have great potential value for fresh use and dehydration and other processed uses.

DETAILED DESCRIPTION OF THE INVENTION

Large quantities of viable true seed from garlic can be produced by growing a parent garlic plant from a virus-free garlic propagule under virus-free conditions. As used herein, the term "large quantities" refers to at least one true seed germinated per plant under sterile conditions. As used herein, "true seed" refers to the embryo and associated food storage and protective structure formed by sexual reproduction. As used herein, "viable" refers to true seed that is capable of germination. "Sexual reproduction," as used herein refers to reproduction by the union of gametes. "Propagule," as used herein refers to true seed, bulbil, clove, or any plant part, tissue or cell from which a new plant can be grown. "Bulbil," as used herein refers to the vegetative reproductive structure formed above ground in the seed head of a garlic plant. "Clove," as used herein refers to the vegetative reproductive structure formed within the garlic bulb. "Bulb," as used herein refers to the storage organ attached to the stem plate of the garlic plant which contains the cloves. "Vegetative reproductive structure," as used herein refers to cloves and other structures formed by asexual reproduction. "Asexual reproduction," as used herein refers to reproduction without the union of gametes. Finally, the term "virus-free," as used herein refers to either the state of the propagule or the manner in which the propagules are grown such that the propagule remains free from virus infection, and in particular, infection by the onion yellow dwarf virus, as can be detected using currently accepted methods.

Virus-free garlic propagules can be produced in any appropriate manner such that the propagule is free from virus infection, and in particular, free from infection by the onion yellow dwarf virus. For example, virus-free garlic propagules can be produced through tissue culture techniques of virus eradication, such as meristem culture, callus culture or thermotherapy. See e.g., Walkey, et al. "Production of Virus-Free Garlic *Allium sativum* L. and Shallot A. Ascalonicum L. By Meristem-Tip Culture," *Journal of Horticultural Science* (1987) 62 (2):211–220; Maksoud, et al., "Garlic Tissue Culture Organogenesis in Callus Culture," *Egypt Journal of Horticulture* (1983) 10 (2):107–114 and Ayuso, et al., "The Elimination of Garlic Viruses by Thermotherapy and/or Tissue Culture," *Cell Biology International Reports*, (1981) 5 (9):835. Virus-free propagules can also be produced through the formation of true seeds or chemical virus remediation of a propagule. See e.g., L. Bos "Viruses and Virus Diseases of Allium Species" *Acta Horticulurae* (1982) 127:11–29.

The virus-free status of a garlic propagule can be determined by the use of any of several widely accepted techniques. These techniques include electron microscopy (EM), Immunosorbent Electron Microscopy (ISEM), or Enzyme-Linked Immunosorbent Assay (ELISA) testing. In California, where virus-free garlic is an item of commerce, the California Department of Food and Agriculture recommends the use of an ELISA test based on the poty virus antisera developed by R. Jordan at the U.S.D.A. Beltsville, and currently marketed by Agdia Inc., Elkhart, Ind.

The virus-free status of these garlic propagules is maintained in any manner such that virus re-infection is avoided. Examples include growing the garlic propagules such that they are spatially or physically isolated from virus infected plants. The necessary spatial isolation depends primarily upon the population densities of the insect vectors of the viruses. In an area of low vector density, a distance of one mile from any known virus infected garlic may be sufficient to prevent re-infection, while in an area with a heavy vector population, it may be necessary to have a five to ten mile buffer from an infected garlic population.

The physical isolation of the virus-free garlic plants can include both natural barriers (such as a mountain range) and artificial barriers (such as screen enclosures); however, the physical isolation is dependent on keeping insect vectors (e.g. aphids) from reaching and re-infecting the plants. If screen enclosures are used to physically isolate the garlic plants, the minimum mesh size necessary to exclude vectors is about 40×40 holes per inch. The preferred mesh size, however, is about 52×52 holes per inch mesh. The mesh can be made of any material as long as it can be maintained free of tears and large holes. Typically, the screen is made of metal, fiberglass, polypropylene or other plastic materials.

Virus-free garlic parent plants are derived from virus-free garlic propagules. These virus-free garlic parent plants are grown to the flowering stage using standard garlic horticultural techniques. For example, the virus-free garlic propagules are planted under isolation conditions in any media which is conducive for growth of the garlic plants such as perlite or natural soil. Water is applied shortly after planting and the ground is watered whenever the soil approaches approximately 70% soil water holding capacity. Nitrogen is also added as is necessary during the growing season. Typically, however, about 300 lbs of nitrogen is applied per acre over the course of a growing season. See "Growing Garlic in California," *Division of Agricultural Sciences*, University of California Leaflet 2948. The garlic plants send up seed stalks approximately 8 months after the initial planting, and flowers begin to open approximately one month to six weeks later.

Once flowers are formed, the flowers are pollinated using any appropriate pollination method. Examples of such pollination methods include manual pollination, self pollination, open pollination and insect pollination.

Those garlic parent plants that are successfully pollinated begin to form true seed. Throughout true seed formation and up to harvest of the viable true seed, the bulbils (or topsets) are not removed, and the flower stalks of the garlic parent plants remain attached to the plant bulbs (without being bound by theory, we have found that removal of the seed stalk from the bulb as is reported in the current literature is detrimental to viable true seed production because such removal separates the seed-producing plant part from a major source of organic nutrients for the seed and also leads to premature desiccation of the seed). In addition, the water and nutrient status is maintained until fully mature true seed is developed even though this is destructive to the bulb. Once mature, viable true seeds are formed, they are harvested in a manner similar to onion seed. See "Onion Production in California," *Division of Agricultural Sciences*, University of California Leaflet 4097, pages 42–43.

Having now generally described the invention, the same will be more readily understood through reference to the following examples which are provided by way of illustration, and are not intended to be limiting of the present invention, unless specified.

EXAMPLE

Comparison of True Seed Production

The greatest success for garlic true seed production is reported by Pooler and Simon in the article, "True Seed Production in Garlic", *Sexual Plant Reproduction* (1994) 7:282–286. In this article, the authors use the following method to produce true seed:

Specifically, 150–200 *A. sativum* and *A. longicuspis* clones from the USDA collection (Pullman, Wash.), Brazil, Germany, Poland, and the former Soviet Union were used. Ten to 20 cloves of each clone were planted between September 15 and October 15 outdoors in cold frames in Kegonsa silt-loam soil in 1987–1992 in Madison, Wis. Garlic plants flowered in mid-June to mid-July. Spathes of all flowering clones were opened manually when vegetative topsets or bulbils, which together with the flowers comprise the umbel, filled out the spathe completely, usually around the time of tetrad formation in microsporogenesis. After opening the spathe, vegetative topsets were removed with fine forceps. Topsets were not removed from approximately 10% of the umbels. Approximately 90% of the flower stems from umbels with topsets removed were cut 10–15 cm above the ground and placed in jars of water, with the remaining flowers left attached to the bulb in the ground. To reduce the deleterious effects of intense sunlight, heat or humidity, cut flower stems were placed under shade cloth outdoors (1989), or in air conditioned greenhouses at 22°–26° C. (1989, 1991–1992) or 16° C. (1990). Some inflorescences were open-pollinated by insect vectors and others were hand pollinated using pollen from pollen-shedding clones. Garlic seeds were harvested in the early fall when the inflorescence dried and were stored at 3° C. Seeds were surface sterilized in 70% ethanol for 1 min, 10% commercial bleach for 1 min, and rinsed in sterile distilled water. Seeds were gently scarified with a scalpel and were placed on sterile solid B-5 medium (Gamborg et al. 1976) without hormones. Seedlings were transplanted to soil at the one-to-two leaf seedling stage and grown in the greenhouse until spring, at which time they were hardened off and planted outdoors.

Using this method, the authors report the recovery of 320 seeds from approximately 500 plants during the 1992 season. These seeds were germinated under sterile conditions, and 49 of the seeds germinated. This gives a germination percentage of 15.5% and a production level of 0.1 germinating seeds per plant.

The genetic material used by Applicant in the experiments run during the 1991 and 1995 seasons was a subset of the material available to Pooler and Simon, and was provided to Applicant by Dr. Simon in his capacity at the USDA. Applicants planted virus-free propagules into prepared beds in mid-September, either in areas that were spatially isolated from virus re-infection or inside screened cages (the screening having a mesh size of about 52×52 holes per inch). Virus-free cloves were planted directly into the native soil at a depth of approximately 1.5 to 2 inches with a spacing between plants of about 1.5 inches and two lines per bed. Virus-free transplants were spaced about 1.5 inches apart, again two lines per bed.

Water was applied shortly after planting and the ground was watered whenever the soil approached 70% soil water holding capacity. Approximately 300 pounds of nitrogen per acre was applied over the course of the growing season, with about half the nitrogen applied pre-plant and the remainder applied in the following spring in two or three applications.

The garlic plants sent up seed stalks between late May and the middle of June. Flowers began to open approximately one month to six weeks later. Bulbils (topsets) were not removed, and the flower stalk was left attached to the intact plant throughout the flowering and seed formation cycle until seed harvest. Pollination was generally accomplished by the use of insects; however, some hand pollinations were performed. Umbels were harvested when the leaves and seed stalk were completely dried and brown. The removed umbels were allowed to dry further, until the capsules holding the seeds began to open and the black seeds started to fall out. At this time, all capsules were threshed and the true seed was removed from the chaff. Seeds that were germinated on sterile media were first surface sterilized and then placed onto sterile solid B-5 medium (Gamborg et al., "Plant tissue culture media", *In Vitro* (1976) 12 (7):473–478). The sterilized seeds were then transferred to fresh B-5 medium every month until the seedling was at the three leave stage, and then it was transferred to a pot filled with perlite. Some seeds were planted directly into pots filled with perlite, and these seeds were not first surface sterilized. The pots with perlite were watered three times a week with nonsterile tap water until the three leaf stage and then they were fertilized once a week with a weak 15-30-15 water soluble fertilizer. Once the seedlings passed the five or six leaf stage, they were hardened off in isolation cages in a greenhouse and then transplanted to either an isolated area or into an isolation cage in a nursery as new virus free propagules.

Using the process described herein, 361 seeds were recovered from 10 plants during the 1991 season. These seeds were also germinated under sterile conditions, and 233 seed germinated. This gives a germination percentage of 64.5% and a production level of 23.3 germinating seeds per plant.

During the 1995 season, the process described herein produced 1377 seeds from 53 plants. These seeds were germinated in perlite in a greenhouse. 490 seeds germinated, giving a germination percentage of 35.6 and a seeds production level of 9.3 viable seed per plant. Even under these more strenuous germination conditions, the disclosed process produced nearly two orders of magnitude more viable seed per plant than the best results reported in the literature.

The results of the above-identified experiments is reported in Table 1 below:

TABLE I

Comparison of True Seed Production

| Year | No. Plants | No. Seeds | Germ. Seeds | Germ. Conditions | % Germination | Germ. Seeds/ Plant |
|---|---|---|---|---|---|---|
| 1992* | ~500 | 320 | 49 | Sterile | 15.5% | 0.1 |
| 1991** | 10 | 361 | 233 | Sterile | 64.5% | 23.3 |
| 1995** | 53 | 1377 | 490 | Perlite | 35.6% | 9.3 |

\* = Results reported in literature for indicated year.
\*\* = Results using the invention as described for indicated year.

Having now fully described this invention, those skilled in the art will appreciate that the same can be performed within a wide range of equivalent parameters, concentrations, and conditions without departing from the spirit and scope of the invention and without undue experimentation. While this invention has been described in connection with specific embodiments thereof, it is capable of further modifications. This specification is intended to cover any variations, uses, or adaptations of the inventions following, in general, the principles of the invention and including such departures from the present disclosure as come within known or customary practice within the art to which the invention pertains and as may be applied to the essential features previously set forth as follows in the scope of the appended claims.

What is claimed is:

1. A process for obtaining large quantities of viable true seed from garlic comprising the steps of:

A. growing a virus-free garlic parent plant from a virus-free garlic propagule under virus free conditions until flowers develop on the garlic plant, the parent garlic plant having a seed stalk which is attached to the plant bulb;

B. pollinating the flowers of the garlic parent plant;

C. providing sufficient water and nutrients to the garlic parent plant to develop mature, viable true seed;

D. leaving the seed stalk of the garlic parent plant attached to the plant bulb until mature, viable true seed is formed; and E. harvesting the true seed.

2. The process of claim 1 in which the virus-free conditions are a result of growing the virus-free propagules spatially apart from virus-infected garlic plants.

3. The process of claim 2 in which the virus-free propagules are grown at least one mile apart from virus-infected garlic plants.

4. The process of claim 1 in which the virus-free conditions are a result of an artificial barrier separating the virus-free propagules from virus-infected garlic plants.

5. The process of claim 4 in which the artificial barrier is a screen enclosure.

6. The process of claim 1 in which the virus-free propagule is a clove.

* * * * *